(12) United States Patent
Robertson

(10) Patent No.: US 9,592,018 B2
(45) Date of Patent: Mar. 14, 2017

(54) DEVICES AND METHODS FOR MINIMALLY INVASIVE REDUCTION OF PARATHYROID ADENOMAS

(71) Applicant: Boston Scientific Scimed, Inc., Maple Grove, MN (US)

(72) Inventor: David W. Robertson, Framingham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 247 days.

(21) Appl. No.: 14/178,101

(22) Filed: Feb. 11, 2014

(65) Prior Publication Data

US 2014/0236145 A1 Aug. 21, 2014

Related U.S. Application Data

(60) Provisional application No. 61/766,522, filed on Feb. 19, 2013.

(51) Int. Cl.

| | |
|---|---|
| *A61B 18/04* | (2006.01) |
| *A61B 6/00* | (2006.01) |
| *A61B 18/14* | (2006.01) |
| *A61B 17/00* | (2006.01) |
| *A61B 18/00* | (2006.01) |

(52) U.S. Cl.
CPC .......... *A61B 6/425* (2013.01); *A61B 6/4057* (2013.01); *A61B 6/4258* (2013.01); *A61B 18/1477* (2013.01); *A61B 2017/00079* (2013.01); *A61B 2018/00702* (2013.01)

(58) Field of Classification Search
CPC ...... A61B 18/1477; A61B 2017/00079; A61B 2018/00702; A61B 6/4057; A61B 6/425; A61B 6/4258
See application file for complete search history.

(56) References Cited

U.S. PATENT DOCUMENTS

| | | | | |
|---|---|---|---|---|
| 4,595,014 A | * | 6/1986 | Barrett | A61B 6/4057 250/363.02 |
| 5,207,672 A | * | 5/1993 | Roth | A61B 18/24 600/439 |
| 5,575,766 A | * | 11/1996 | Swartz | A61M 25/0041 600/16 |
| 5,846,513 A | * | 12/1998 | Carroll | A61B 6/4057 250/336.1 |
| 6,086,585 A | * | 7/2000 | Hovda | A61B 18/1402 128/898 |
| 7,914,442 B1 | * | 3/2011 | Gazdzinski | A61B 1/00009 600/109 |
| 2001/0002250 A1 | * | 5/2001 | Burbank | A61B 17/00491 424/9.5 |
| 2002/0026127 A1 | * | 2/2002 | Balbierz | A61B 18/1206 600/567 |

(Continued)

*Primary Examiner* — Daniel Fowler
(74) *Attorney, Agent, or Firm* — Bookoff McAndrews, PLLC

(57) ABSTRACT

Apparatus and methods for performing glandular reduction are described. In an example embodiment, an apparatus includes a needle-like probe containing a scintillation detector for converting gamma and x-rays emitted from a radio-labeled gland into photons that are then carried from the probe through a fiberoptic cable to a photodetector, and a therapy element for causing selective tissue destruction by directing energy toward the radio-labeled gland.

20 Claims, 2 Drawing Sheets

(56) References Cited

U.S. PATENT DOCUMENTS

2007/0032826 A1* 2/2007 Schwartz ............ G06F 19/3437
  607/2
2008/0237028 A1* 10/2008 Kislev .................... A61B 8/481
  204/157.15
2009/0127459 A1* 5/2009 Neustadter ............. A61B 19/52
  250/336.1

* cited by examiner

DEVICES AND METHODS FOR MINIMALLY INVASIVE REDUCTION OF PARATHYROID ADENOMAS

CLAIM OF PRIORITY

This application claims the benefit of priority under 35 U.S.C. §119(e) of U.S. Provisional Patent Application Ser. No. 61/766,522, filed on Feb. 19, 2013, which is herein incorporated by reference in its entirety.

BACKGROUND

Current surgical methods of parathyroidectomy involve a 1-2 cm incision in the neck for exposure and removal of an adenoma-containing or hyperplastic parathyroid gland. Current minimally invasive techniques may identify and locate a radio-labeled gland using intra-operative gamma detection probes and visualization guided removal of the gland using an endoscopic instrument. There is a need for a less invasive method of reducing the abnormal function of the hyperplastic parathyroid gland.

DETAILED DESCRIPTION

Described herein is a system and method for performing parathyroid adenoma reduction. In an example embodiment, a system includes a needle-like probe (e.g., similarly sized to current breast vacuum suction biopsy needles) containing a scintillation detection element for converting gamma and x-rays emitted from a radiolabeled gland into photons (e.g. cadmium telluride scintillation crystal) that are then carried from the probe through a fiberoptic cable to a photodetector/analyzer, and a therapy element for causing selective tissue destruction by directing energy toward the parathyroid adenoma. The therapy element may include one or more energy sources that deliver energy to the tissue in the form of RF thermal energy, high intensity or thermal ultrasound, DC voltage induced irreversible electroporation, or other forms. The needle probe may be inserted percutaneously under local anesthesia and iteratively directed into the target gland by use of the scintillation crystal within the probe to detect the strongest concentration of gamma rays being emitted by the radio-labeled gland. The adenoma may then be necrosed in situ by the directed energy emitters mounted on the needle. Positioning of the probe to the target tissue may be aided by internal or external gamma ray shields with one or more slots or holes that may be rotated or moved along the shaft of the needle in order to discern the direction of the strongest gamma emissions.

Figure 1:
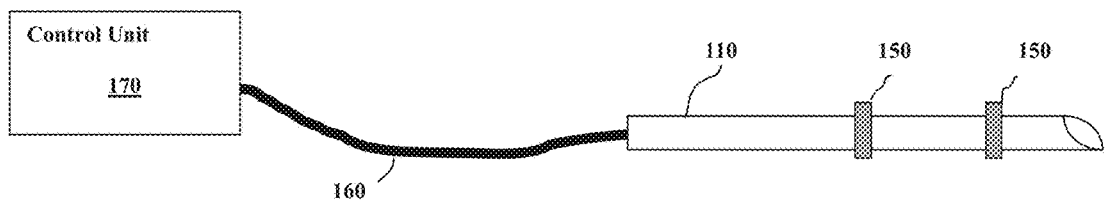
FIG. 1 shows an example system that includes a control unit and a probe.

FIG. 1 shows an example system that includes a needle probe 110 and a control unit 170. The needle probe has two therapy elements 150 mounted thereon that may be, for example, electrodes for delivering electrical energy to the target tissue. The needle probe 110 is connected to the control unit by a cable 160. The cable 160 contains a fiber optic cable for conveying photons from a scintillation detection element in the needle probe to a photon detector in order to measure radiation emitted from the radioactive label. The cable 160 also contains wires for connecting the therapy elements 150 to actuation circuitry (e.g., a voltage source) in the control unit that energizes and/or controls the therapy elements.

Figure 2:
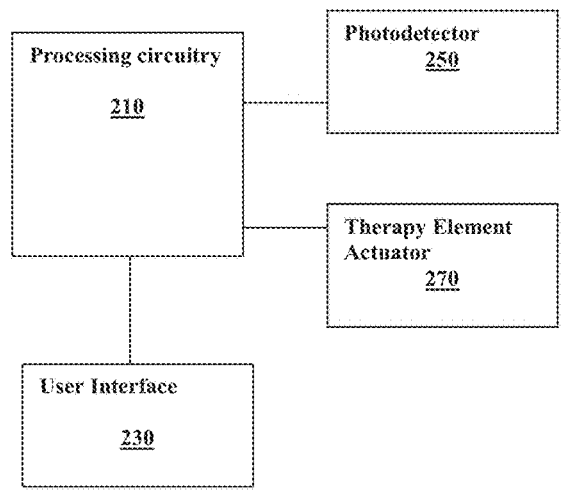
FIG. 2 shows example components of the control unit.

FIG. 2 shows the basic components of an example control unit 170. Processing circuitry 210, which may include a processor and associated memory, is connected to a photodetector 250 and therapy element actuator 270. The photodetector generates a voltage signal proportional to the intensity of the photons conveyed thereto via fiber optic cable from the scintillation detector, which voltage signal is then used by the processing circuitry to measure the radiation emitted from the radio-labeled gland. The therapy element actuator 270 powers and/or controls the therapy elements 150 mounted on the needle probe to cause energy to be directed toward the target tissue. A user interface 230 is also connected to the processing circuitry that provides information to an operator such as radiation measurement and provides a user input for controlling the therapy element actuator. In certain embodiments, the user interface connects directly to the therapy element actuator 270.

Figure 3:
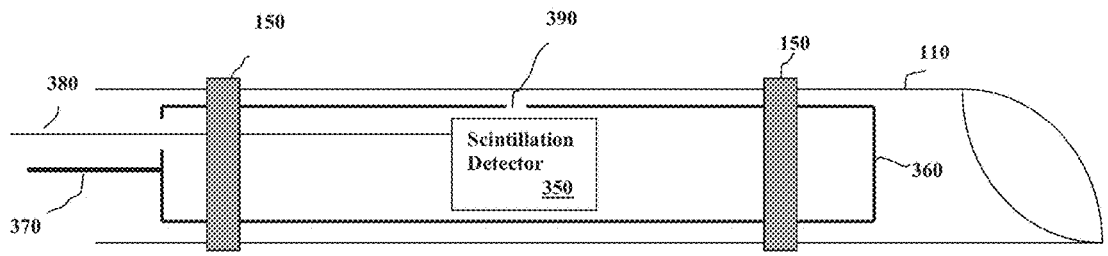
FIG. 3 shows example components of the probe.

FIG. 3 shows the basic components of an example needle probe 110 in more detail. Two therapy elements 150 are shown as mounted on the exterior of the probe. Other embodiments may utilize a different number of therapy elements (e.g., one) that may be mounted externally or internally. A scintillation detector 350 is shown as being positioned in the interior of the probe between the two therapy elements 150. A fiber optic cable 380 runs through the interior of the probe to connect the scintillation detector to the photodetector 250 in the control unit. In this embodiment, a cylindrical radiation shield 360 made of a material impervious to radiation (e.g., lead) surrounds the scintillation detector 350. The shield 360 is rotatably and slidably mounted within the probe and connected to a rod 370 which may be operated manually (or, in some embodiments, operated by a robotic manipulator) to cause rotation or longitudinal movement of the shield. An aperture 390 in the shield allows radiation to reach the detector 350. As the aperture 390 is rotated or moved longitudinally along the axis of the probe, the radiation may be measured in order to facilitate the proper positioning of the probe for delivering therapy to the radio-labeled gland.

Figure 4:
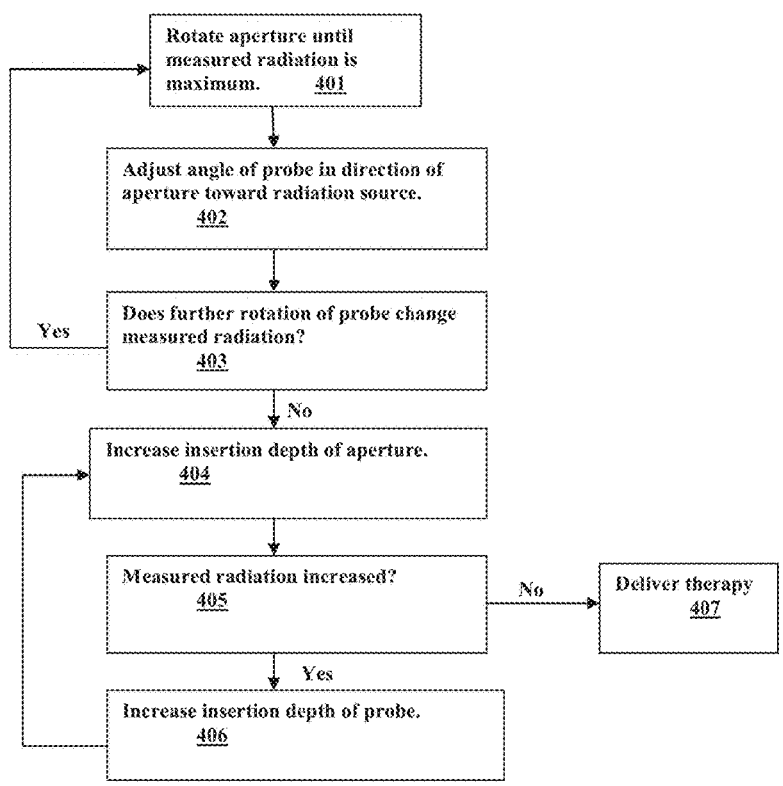
FIG. 4 illustrates an example algorithm for positioning the probe.

FIG. 4 illustrates a basic algorithm for positioning the probe that utilizes the moveable aperture. The algorithm could be performed manually by an operator or, in another embodiment, by the control unit where the processing circuitry is interfaced to a robotic manipulator connected to the rod 370. The probe 110 is first positioned for insertion into the target tissue. At step 401, the aperture is rotated until the radiation measured from the radiation source (i.e., the radio-labeled gland) is at a maximum. At step 402, the angle of the probe is then adjusted toward the direction that the aperture faces (i.e., toward the radiation source). At step 403, the aperture is again rotated while the radiation is measured. If the probe is pointing directly at the radiation source, no change in measured radiation will be detected as the aperture is rotated. If a change in measured radiation is detected while rotating the aperture, steps 401 through 403 are repeated. Otherwise, at step 404, the insertion depth of the aperture is increased by moving the aperture longitudinally toward the radiation source. If no increase in measured radiation is detected at step 405, it may be surmised that the probe is inserted at a proper depth within the target tissue so that therapy can be delivered at step 407. Otherwise, the insertion depth of the probe is increased at step 406, and steps 404 and 405 are repeated.

In an example embodiment, an apparatus comprises: a probe for inserting into a body tissue containing a radio-labeled target tissue; a scintillation detector within the probe; a therapy element incorporated into the probe for delivering energy to the target tissue; a control unit that includes a therapy element actuator and processing circuitry connected to a photodetector; a cable containing a fiber optic cable connecting the photodetector to the scintillation detector and wires connecting the therapy element actuator to the therapy element; wherein the processing circuitry is configured to measure the radiation emitted by the target tissue from signals generated by the photodetector; and, wherein the therapy element actuator is operable to cause delivery of energy by the therapy element to the target tissue. The apparatus may further comprise a radiation shield surrounding the scintillation detector within the probe that has an aperture for allowing radiation to reach the scintillation detector, wherein the radiation shield may be rotated and longitudinally translated along the axis of the probe to aid in positioning the probe in proximity to the target tissue. The apparatus may further comprise a robotic manipulator operated by the processing circuitry, wherein the processing circuitry is programmed to: (a) rotate the aperture until the radiation measured is at a maximum; (b) adjust an insertion angle of the probe toward the direction that the aperture faces; and, (c) rotate the aperture while the radiation is measured and repeat steps (a) and (b) until no change in the measured radiation is detected. The processing circuitry may be further programmed to: (a) increase the insertion depth of the aperture by moving the aperture longitudinally within the probe toward the target tissue; (b) measure radiation from the target tissue and, if an increase in measured radiation is detected after increasing the insertion depth of the aperture, increase the insertion depth of the probe; and, (c) repeat steps (a) and (b) until no increase in measured radiation is detected at step (b) and then initiate delivery of energy from the probe. The therapy element may be a voltage source for delivering radio-frequency electrical energy, a voltage source for delivering direct current electrical energy, or an ultrasonic transducer. The apparatus may further comprise a user interface connected to the processing circuitry, wherein the user interface provides information to an operator relating to radiation measurement and/or a user input for controlling the therapy element actuator.

An example method for parathyroid adenoma reduction in a patient, comprises: radio-labeling the parathyroid adenoma as a target tissue; inserting a probe into the patient toward the target tissue; measuring radiation emitted by the target tissue using a scintillation detector within the probe that conveys photons to a photodetector via a fiber optic cable; positioning the probe in proximity to the target tissue based upon the measured radiation; and, delivering energy from the probe to the target tissue to cause necrosis. The method may further comprise guiding the probe to the target tissue by rotating and longitudinally translating a radiation shield surrounding the scintillation detector within the probe that has an aperture for allowing radiation to reach the scintillation detector. The method may further comprise: (a) rotating the aperture until the radiation measured is at a maximum; (b) adjusting an insertion angle of the probe toward the direction that the aperture faces; and, (c) rotating the aperture while the radiation is measured and repeating steps (a) and (b) until no change in the measured radiation is detected. The method may further comprise: (a) increasing the insertion depth of the aperture by moving the aperture longitudinally within the probe toward the target tissue; (b) measuring radiation from the target tissue and, if an increase in measured radiation is detected after increasing the insertion depth of the aperture, increasing the insertion depth of the probe; and, (c) repeating steps (a) and (b) until no increase in measured radiation is detected at step (b) and then initiating delivery of energy from the probe.

Embodiments relating to further particularizations and features have been described above. It should be appreciated that those embodiments may also be combined in any manner considered to be advantageous. Also, many alternatives, variations, and modifications will be apparent to those of ordinary skill in the art. Other such alternatives, variations, and modifications are intended to fall within the scope of the following appended claims.

What is claimed is:

1. A method of glandular reduction in a patient, comprising:
   marking a gland as a target tissue with a material that emits energy;
   inserting a probe into the patient and the target tissue, wherein inserting the probe includes:
     measuring energy emitted from the marked target tissue using a detector within the probe,
     positioning the probe in proximity to the target tissue based upon the measured energy, and
     guiding the probe to the target tissue by rotating and longitudinally translating a shield surrounding the detector, wherein the shield blocks the energy, the rotating and longitudinal translating of the shield takes place within the probe, and the shield has an aperture for allowing the energy to reach the detector; and
   delivering therapy energy from a therapy element of the probe to the target tissue.

2. The method of claim 1 wherein the detector is a scintillation detector, and the method further comprises conveying photons from the scintillation detector to a photodetector via a fiber optic cable.

3. The method of claim 1 further comprising delivering the therapy energy from the therapy element in a manner to cause necrosis of the target tissue.

4. The method of claim 1 further comprising:
   (a) rotating the aperture until the measured energy is at a maximum, wherein the aperture is rotated within the probe;
   (b) adjusting an insertion angle of the probe toward the direction that the aperture faces; and,
   (c) rotating the aperture while the energy is measured, wherein the aperture is rotated within the probe, and repeating steps (a) and (b) until no change in the measured energy is detected and a central longitudinal axis of the probe extends toward the target tissue.

5. The method of claim 4 further comprising, after the insertion angle of the probe is adjusted so that the central longitudinal axis of the probe extends toward the target tissue:
   (a) increasing the insertion depth of the aperture by moving the aperture longitudinally within the probe toward the target tissue;
   (b) measuring the energy from the target tissue and, if an increase in the measured energy is detected after increasing the insertion depth of the aperture, increasing the insertion depth of the probe; and,
   (c) repeating steps (a) and (b) until no increase in the measured energy is detected at step (b) and then initiating delivery of the therapy energy from the probe.

6. The method of claim 5 wherein the positioning of the probe is performed by a robotic manipulator.

7. The method of claim 5 wherein the rotation and translation of the shield is performed by a robotic manipulator.

8. The method of claim 1 wherein the target tissue is a parathyroid adenoma.

9. The method of claim 1 wherein delivering the therapy energy to the target tissue includes delivering, to the target tissue from a voltage source, one of radio-frequency electrical energy and direct current electrical energy.

10. The method of claim 1 wherein the therapy element is an ultrasonic transducer.

11. The method of claim 1 wherein marking the gland includes radio-labeling the gland such that radiation is emitted from the radio-labeled gland.

12. An apparatus, comprising:
a probe for inserting into a body tissue containing a target tissue marked with a material that emits energy;
a detector within the probe;
a therapy element incorporated into the probe for delivering therapy energy to the target tissue;
a control unit that includes a therapy element actuator and processing circuitry connected to a photodetector;
wherein the processing circuitry is configured to measure the energy emitted from the marked target tissue from signals generated by the photodetector;
wherein the therapy element actuator is operable to cause delivery of the therapy energy by the therapy element to the target tissue; and
a shield surrounding the detector to block the energy, wherein the shield is within the probe, the shield has an aperture for allowing the energy to reach the detector, and the shield is rotatable and longitudinally translatable within the probe to facilitate positioning of the probe in proximity to the target tissue.

13. The apparatus of claim 12 wherein the shield is rotatable and longitudinally translatable along a longitudinal axis of the probe to facilitate positioning of the probe in proximity to the target tissue.

14. The apparatus of claim 13 further comprising a robotic manipulator operated by the processing circuitry, wherein the processing circuitry is programmed to:
(a) rotate the aperture until the energy measured is at a maximum, wherein the aperture is rotated within the probe;
(b) adjust an insertion angle of the probe toward the direction that the aperture faces; and,
(c) rotate the aperture while the energy is measured, wherein the aperture is rotated within the probe, and repeat steps (a) and (b) until no change in the measured energy is detected and a central longitudinal axis of the probe extends toward the target tissue.

15. The apparatus of claim 14 wherein, after the insertion angle of the probe is adjusted so that the probe points toward the target tissue, the processing circuitry is programmed to:
(a) increase the insertion depth of the aperture by moving the aperture longitudinally within the probe toward the target tissue;
(b) measure the energy from the target tissue and, if an increase in measured energy is detected after increasing the insertion depth of the aperture, increase the insertion depth of the probe; and,
(c) repeat steps (a) and (b) until no increase in the measured energy is detected at step (b) and then initiate delivery of the therapy energy from the probe.

16. The apparatus of claim 12 wherein the therapy element is operatively coupled to a voltage source for delivering at least one of radio-frequency electrical energy and direct current electrical energy to the target tissue.

17. The apparatus of claim 12 wherein the therapy element is an ultrasonic transducer.

18. The apparatus of claim 12 further comprising a user interface connected to the processing circuitry for at least one of providing information to an operator relating to the energy measurement, and for controlling the therapy element actuator.

19. The apparatus of claim 12 wherein the therapy element includes at least two electrodes, and the detector and the aperture are located between the electrodes.

20. An apparatus, comprising:
a probe for inserting into a body tissue containing a target tissue marked with a material that emits energy, wherein the probe has a closed distalmost end;
a detector within the probe;
a therapy element incorporated into the probe for delivering therapy energy to the target tissue; and
a shield surrounding the detector to block the energy, wherein the shield is within the probe, the shield has an aperture for allowing the energy to reach the detector, and the shield and the aperture are rotatable and longitudinally translatable within the probe to facilitate positioning of the probe in proximity to the target tissue.

* * * * *